US00PP13286P3

(12) United States Plant Patent

Kester et al.

(10) Patent No.: US PP13,286 P3

(45) Date of Patent: Nov. 26, 2002

(54) ALMOND TREE NAMED 'WINTERS'

(75) Inventors: Dale E. Kester, Davis, CA (US); Thomas M. Gradziel, Davis, CA (US); Richard N. Asay, Thayne, WY (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/838,203

(22) Filed: Apr. 20, 2001

(65) Prior Publication Data

US 2002/0157144 P1 Oct. 24, 2002

(51) Int. Cl.[7] ..... A01H 5/00

(52) U.S. Cl. ..... Plt./155

(58) Field of Search ..... Plt./155

*Primary Examiner*—Bruce R. Campell

*Assistant Examiner*—Susan B. McCormick

(74) *Attorney, Agent, or Firm*—Burns, Doane, Swecker & Mathis, LLP

(57) ABSTRACT

An improved *Prunus dulcis* variety is provided that is well suited for serving as a pollenizer for the widely-grown 'Nonpareil' variety (non-patented in the United States). Good bloom overlap in combination with good production quality is displayed. The tree exhibits an upright and spreading growth habit. Abundant lateral vegetative growth is produced on current season shoots which makes possible high tree productivity. Desirable fruit and kernel characteristics for shelled and possessed almond production are displayed.

2 Drawing Sheets

BOTANICAL/COMMERCIAL CLASSIFICATION

Figure 1:
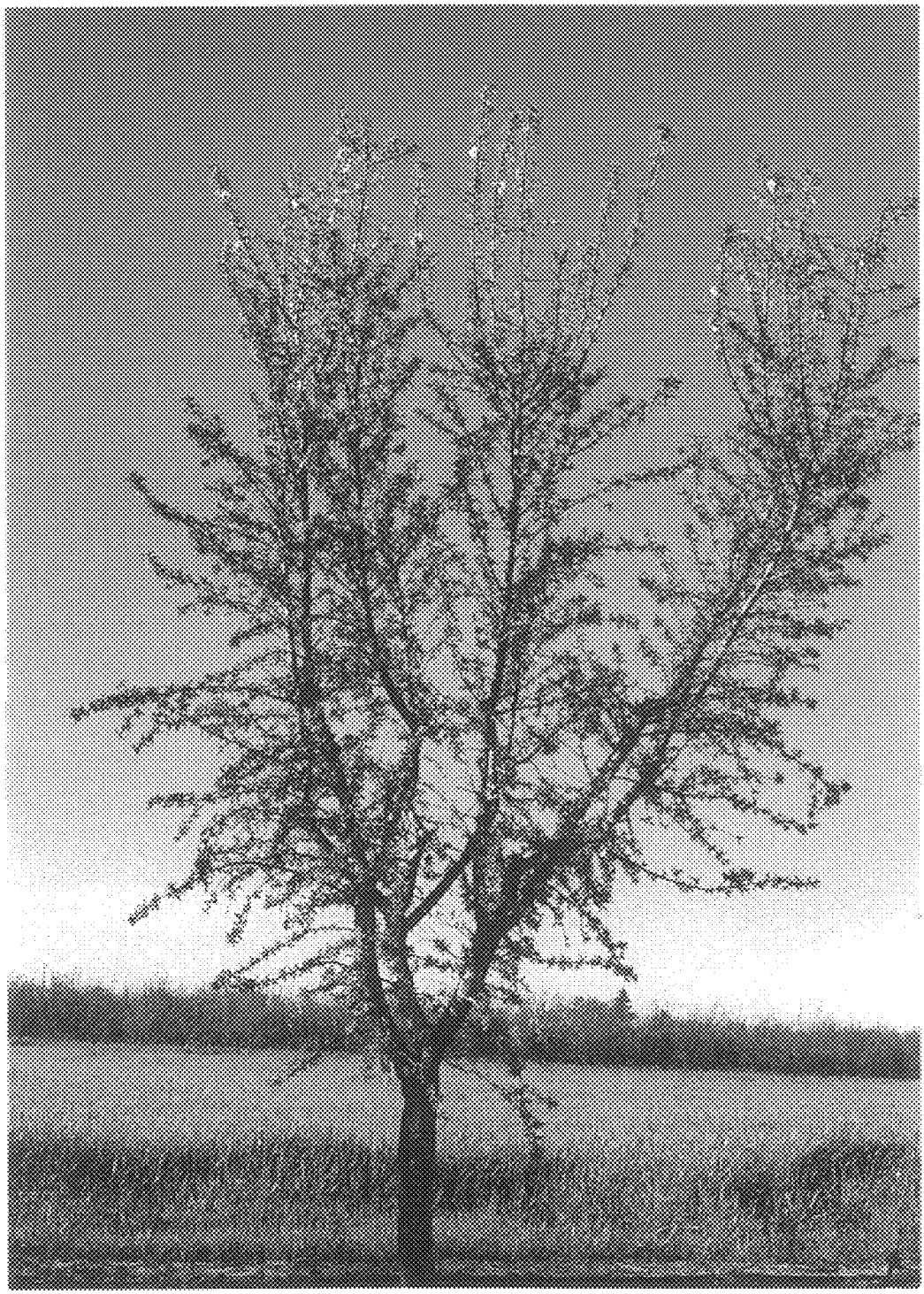

*Prunus dulcis*/Almond Tree.

VARIETAL DENOMINATION

'Winters'.

SUMMARY OF THE INVENTION

The 'Nonpareil' almond variety (non-patented in the United States) is recognized to form an almond crop of high market quality. During 1999 it is estimated that approximately 41 percent of total California, U.S.A., almond acreage was planted with the 'Nonpareil' variety. Since the 'Nonpareil' variety is self-sterile, it is essential for almond growers to provide a nearby pollen source from a cross-compatible almond variety. Since the early 'Nonpareil' bloom contains the highest proportion of viable flowers, it is crucial to provide ample pollen from an appropriate source at this time to assure a maximum crop set. Traditional almond pollenizers such as the 'Ne Plus Ultra' variety (non-patented in the United States) and the 'Solano' variety (non-patented in the United States) often bloom too early to have good overlap with the flowering of the 'Nonpareil' variety. The breeding program that resulted in the creation of the new variety of the present invention was carried out at the Wolfskill Experimental Orchard of the University of California located near Winters, Calif., U.S.A. The cross that produced the new variety of *Prunus dulcis* of the present invention can be summarized as follows:

Selection 3-1×Selection 6-27.

Selection 3-1 possessed the following pedigree:

'Peerless'×'Harpareil' {'Harriot'×'Nonpareil'}.

Selection 6-27 possessed the following pedigree:

'Nonpareil'×'Jordanolo' {'Harriot'×'Nonpareil'}.

Each of the plants leading to the creation of the new variety is non-patented in the United States.

The progeny of the above cross were carefully observed and studied. Such study resulted in the selection of the variety of the present invention. It was found that a single plant of the new variety of the present invention resulted from such controlled breeding and such plant has been carefully preserved in view of its highly desirable combination of characteristics. Thermotherapy treatment was used to eliminate viruses once initial virus indexing provided a positive indication for Prunus Ring Spot Virus.

It was found that the new *Prunus dulcis* variety of the present invention possesses the following combination of characteristics:

(a) Displays good bloom overlap with the 'Nonpareil' variety and is cross-compatible with the 'Nonpareil' variety, (b) Exhibits an upright and spreading growth habit, (c) Produces abundant lateral vegetative growth on current season shoots which makes possible high tree productivity, and (d) Exhibits desirable fruit and kernel characteristics for shelled and processed almond production.

The new variety generally provides more fruiting wood than the 'Nonpareil' variety. The fruit hangs well on the tree and is easy to harvest. Such harvest commonly occurs approximately 3 to 4 weeks after that of the 'Nonpareil' variety. An improved pollenizer for the 'Nonpareil' variety is provided.

The new variety of the present invention has been asexually reproduced by budding and grafting at Davis, Calif., U.S.A. and at Parlier, Calif., U.S.A. Such propagation has confirmed that the characteristics of the new variety are stable and are reliably transmitted to subsequent generations.

It should be understood that the inherently exhibited characteristics of the new variety described herein may vary somewhat when grown under differing climatic and growing conditions.

Initially the new variety was designed as breeding line 13-1 and subsequently has been named 'Winters'.

BRIEF DESCRIPTION OF THE PHOTOGRAPHS

The accompanying photographs show representative specimens of the new variety at Winters, Calif., U.S.A., as depicted in color as nearly true as is possible to make the same in color illustrations of this character. The trees were grown on Nemaguard rootstock.

FIG. 1 shows a typical approximately five year-old tree of the new variety on Mar. 10, 2000.

Figure 2:
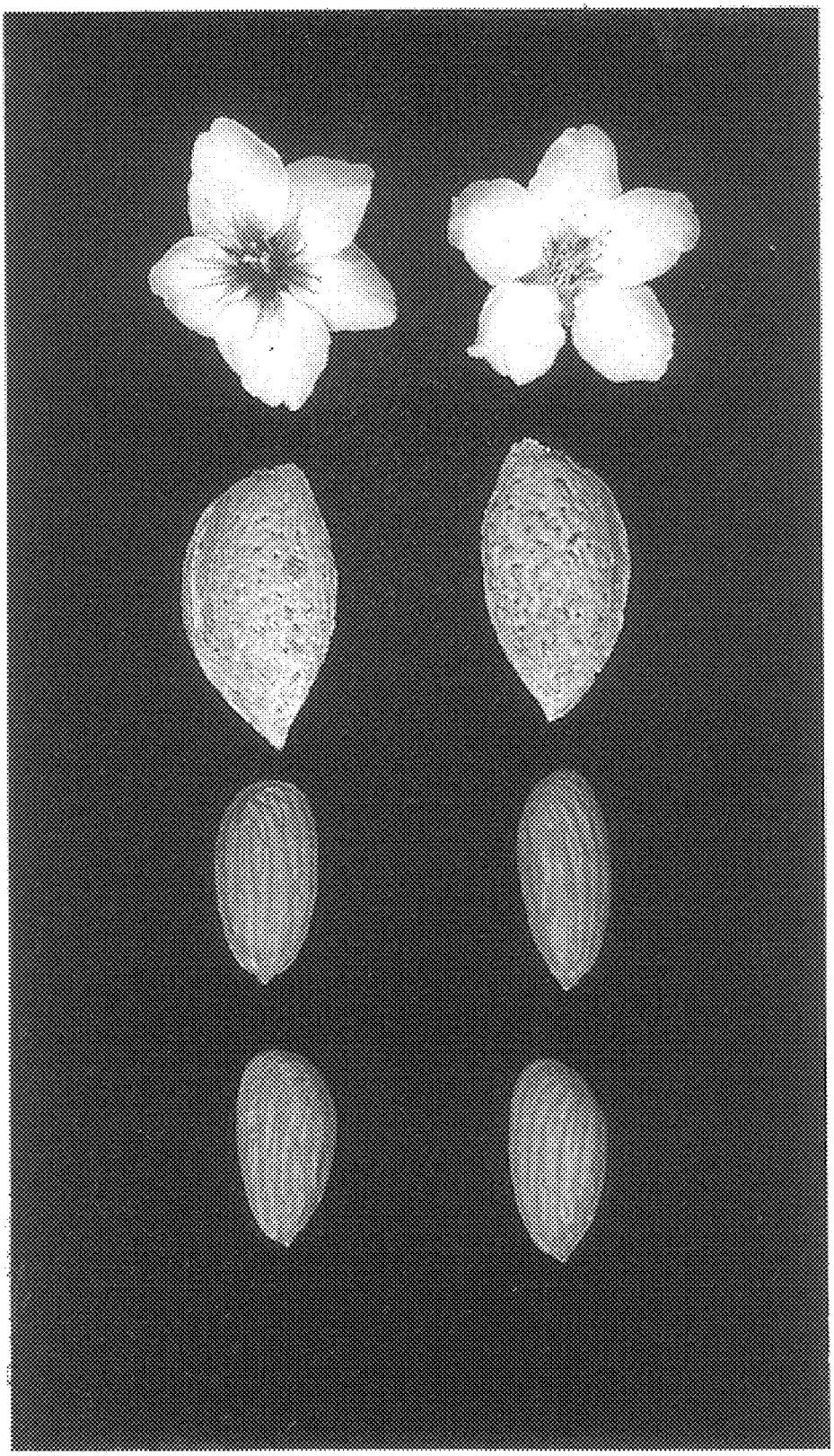

FIG. 2 shows typical flowers, nuts and kernels of the new variety on Feb. 24, 2000. The flower on the left is approximately 6 days more mature than the flower on the right, with the red coloration at the base of petals intensifying with age. The seeds had been harvested on Oct. 14, 1999.

DETAILED DESCRIPTION

The following is a detailed description of the new 'Winters' variety when observed during the 1999 and 2000 growing seasons at the Wolfskill Experimental Orchard of the University of California located near Winters, Calif., U.S.A., and at Davis, Calif., U.S.A. During 2000 the trees were approximately five years of age. The trees were grown on Nemaguard rootstock. Color designations are provided by reference to the "Dictionary of Color" by Maerz and Paul, First Edition (1930).

Tree:

*Size.*—Large. Similar to that of the 'Nonpareil' variety. A typical six year-old tree of the 'Winters' variety commonly has a height of approximately 7.3 m and a width of approximately 6.1 m.

*Vigor.*—Moderate. Approximately 0.5 to 0.8 m of terminal shoot growth commonly is observed per season.

*Density.*—Open.

*Form.*—Upright to spreading and somewhat bushy, and more upright than the 'Nonpareil' variety.

Trunk:

*Diameter.*—Medium, and commonly approximately 17 cm measured 30 cm above the soil line.

*Texture.*—Typical of the species, and rough and flaky.

Branches:

*Form.*—Relatively straight with the current year laterals typically at near the mid-section of longer shoots.

*Texture.*—The relatively slender shoots have smooth glossy surfaces with horizontal lenticels.

*Length.*—Approximately 10 to 30 cm.

*Diameter.*—Approximately 7 mm at the terminal ends of one year-old branches.

*Nodes.*—Approximately 9 to 27 per branch depending upon the length.

*Internodes.*—Approximately 1 to 2 cm in length.

*Shoot color.*—Medium green (20-L-2) with a reddish flush (7-L-10).

*Buds.*—Terminal buds are short, and the lateral buds are conical and pointed with dark brown scales (8-J-7). Double buds sometimes are present at a node.

*Scales.*—Generally dark brown (8-J-7) and nondistinctive.

*Spurs.*—Generally numerous, short and stubby, and approximately 1 cm in length.

*Lateral buds.*—Rounded, brown in coloration, and approximately 2 to 5 per branch and eventually will become flower buds.

*Epidermis.*—On one year old spurs, green coloration (19-K-4) is displayed with the shorter spurs tending to be considerably darker in coloration.

*Terminal buds.*—Small, pointed and very dark in coloration.

*Two year-old wood.*—Reddish brown (15-C-12) in coloration.

*Three year-old wood.*—Lighter brown (15-C-9) in coloration. Commonly numerous persistent peduncles are present from fruit that was borne on previous years. Stem scars are prominent.

*Four year-old wood.*—Dull grayish-brown (15-A-6) in coloration where the epidermis has sloughed off. Such coloration is not particularly distinctive. Some spurs continue to produce, but many spurs appear with clusters of persistent peduncles from earlier production.

*Lenticels.*—Orange-brown (12-J-9) in coloration, and typically number approximately 4 to 5 per $cm^2$ on five year-old wood.

Leaves:

*Size.*—Variable and commonly approximately 24 to 79 mm in length, and approximately 15 to 25 mm in width, and flat.

*Ratio of blade width to blade length.*—Commonly approximately 0.22:1.

*Quantity.*—Abundant with approximately eight leaves per current-season spur.

*Configuration.*—Lanceolate and occasionally elliptical, and commonly taper to the apex at approximately one-third of the length from the apex.

*Tip.*—Acuminate, and tapers to a more or less acute tip.

*Base.*—Generally rounded to oblique.

*Petiole.*—Approximately 1.6 cm in length and approximately 1.3 mm in diameter at the base of a fully expanded leaf. The coloration is 17-J-3.

*Ratio of petiole length to leaf length.*—Commonly approximately 0.27:1.

*Color.*—The top surface commonly is 24-L-4 and the under surface commonly is 22-K-6.

*Margins.*—Crenate with generally shallow crenations.

*Venation.*—Pinnately net-veined, and 17-F-1 in coloration.

*Glands.*—Small in size (approximately 0.5 mm), globose, commonly two alternate on the petiole and primarily at the base of the leaf. Orange-brown (7-C-12 to 13-B-11) in coloration.

Flowers:

*Blooming period.*—Typically starts approximately 4 to 6 days prior to the 'Nonpareil' variety with full bloom occurring when the 'Nonpareil' variety is at approximately 90 percent bloom. A typical bloom commonly lasts approximately 17 days and approximately 3 days longer than the 'Nonpareil' variety.

*Quantity of bloom.*—Heavy.

*Color.*—3-A-1 on both surfaces with reddish pink (49-J-10) developing at the petal claw and at the petal base as the flower ages.

*Petal apex.*—Retuse, rounded, and commonly with 1 to 3 shallow notches.

*Petal base.*—Rounded and smooth to slightly crenate.

*Petal texture.*—Soft, velvety, and with slight puckering at the margins.

*Petal number.*—Commonly 5; however, approximately 2 percent of the flowers may contain 4, or 6 or more petals.

*Pollen.*—Is cross-compatible with the 'Nonpareil' variety and the 'Carmel' variety (non-patented in the United States) and is well capable of serving as a pollinizer for such varieties.

*Fruit stems.*—Commonly approximately 6 mm in length, approximately 3 mm in diameter, and bear a coloration of 19-K-7.

Crop:

*Bearing.*—Regular Bearer. Bearing occurs predominantly from spurs which are two years old or older. Fruit production occurs on a combination of spurs and terminal shoots, including a lateral bearing habit on abundant approximately perpendicular lateral branches developed during the previous season. This generally results in greater total fruiting wood compared to the 'Nonpareil' variety.

*Production.*—Heavy. A well-maintained orchard of 6 year-old trees will yield approximately 2200 pounds per acre of harvested nuts which have been removed from the hulls.

*Distribution.*—The crop is well distributed on the tree.

*Tenacity.*—Hangs well on the tree and is easy to harvest.

*Harvest period.*—Late and typically approximately 3 to 4 weeks after the 'Nonpareil' variety.

*Storage character.*—Dried fruit and nuts can be stored for over one year.

Immature fruit:

*Size.*—Approximately 3.8 cm in length and approximately 2.4 cm in width at the suture line.

*Side view.*—Uniformly elongate.

*Dorsal eagle.*—Straight but sharply curving at the apical and the basal ends which results in a more or less straight line across both the basal and the apical ends.

*Ventral edge.*—Uniformly curving along the entire length.

*Basal end.*—Generally flat.

*Apical end.*—With a small, short, acute protruding tip.

*Dorsal view.*—Both sides very uniform, and uniformly slightly curving.

*Ridge.*—Inconspicuous.

*Ventral view.*—Similar to the dorsal view with an inconspicuous uniformly curving ventral line.

*Apical end view.*—Rounded with a very slight inconspicuous ridge.

*Basal view.*—Rounded with a noticeable suture line.

*Base scar.*—Round, medium in size, and detaches relatively easily with a clean separation.

*Dehiscence.*—Begins at the dorsal edge and eventually extends to the dorsal edge.

*Pubescence.*—Whitish (18-C-2), very fine and uniform over a medium green (19-I-5) surface.

Hull:

*Outer surface.*—Smooth and pubescent.

*Form.*—Uniform and symmetrical.

*Shape.*—Oval in longitudinal section.

*Thickness.*—Generally 2 to 2.5 mm when dry.

*Flesh.*—Tough but brittle when dry.

*Suture.*—Medium.

*Color.*—Light green (21-J-6).

*Dehiscence.*—Opens freely.

*Splitting.*—Along suture.

*Nut cavity.*—Oval.

*Adherence.*—Hulls are easily removed from nuts by mechanical hullers.

Nut:

*Size.*—Medium to large, and commonly approximately 2.25 cm in length and approximately 1.07 cm in width on average.

*Shape.*—Elongated as illustrated in FIG. 2.

*Shell thickness.*—Paper (i.e., easily cracked).

*Outer color.*—Medium light brown (12-I-7).

*Inner color.*—Medium brown (12-H-8).

*Pitting.*—Few in number, large, deep and round.

*Base.*—Ventrally oblique.

*Stem scar.*—Medium in size and obtuse.

*Apex.*—Obtuse.

*Wing.*—Broad and thin and tapered toward the base.

*Ventral streak.*—Narrow and light brown (12-H-8) in coloration.

*Percentage of kernel to nut.*—Approximately 57 percent.

Kernel:

*Size.*—Similar to that of the 'Nonpareil' variety but slightly smaller. Commonly approximately 24 mm in length, 11 mm in width, and 7 mm in thickness. The average weight commonly is approximately 1.1 gram.

*Configuration.*—Elongated and flat.

*Base.*—Ventrally oblique.

*Stem scar.*—Large and obtuse.

*Apex.*—Acuminate.

*Texture.*—Wrinkled and furrowed as illustrated in FIG. 2, and otherwise smooth with veins.

*Pellicle.*—Medium in size.

*Color.*—Light brown (13-J-10) with red-brown veins (6-F-12).

*Number of doubles.*—Low and commonly less than 10 percent.

*Flavor.*—Sweet.

*Quality.*—Good.

*Blanching.*—Is blanchable.

Cultural characteristics:

*Resistance to insects.*—Comparable to that of the 'Nonpareil' variety. The more open shell structure in 'Winters' may possibly lead to greater worm damage of the kernel.

*Susceptibility to bud failure.*—Low.

*Susceptibility to diseases.*—Is susceptible to Anthracnose and Alernaria Leaf Spot.

We claim:

1. A new and distinct *Prunus dulcis* tree having the following combination of characteristics:

(a) Displays good bloom overlap with the 'Nonpareil' variety and is cross-compatible with the 'Nonpareil' variety, (b) Exhibits an upright and spreading growth habit, (c) Produces abundant lateral vegetative growth on current season shoots which makes possible high tree productivity, and (d) Exhibits desirable fruit and kernel characteristics for shelled and processed almond production;

substantially as herein shown and described.

* * * * *